United States Patent [19]

Horak et al.

[11] Patent Number: 4,460,747

[45] Date of Patent: * Jul. 17, 1984

[54] SURFACE MODIFIED POLYMERS

[75] Inventors: Vaclav Horak, Bethesda, Md.; Jiri Janata, Salt Lake City, Utah

[73] Assignee: The University of Utah, Salt Lake City, Utah

[*] Notice: The portion of the term of this patent subsequent to Sep. 22, 1998 has been disclaimed.

[21] Appl. No.: 296,924

[22] Filed: Aug. 27, 1981

Related U.S. Application Data

[63] Continuation-in-part of Ser. No. 027,366, Apr. 5, 1979, Pat. No. 4,291,133.

[51] Int. Cl.³ .................. C08L 33/10; C08L 23/06; C08L 27/06
[52] U.S. Cl. .................................. 525/197; 525/227; 525/194; 525/186; 525/241; 525/240; 525/239; 525/238; 525/232; 427/307; 428/515; 428/407
[58] Field of Search ............... 427/307; 523/351; 521/54; 525/186, 68, 70, 227, 232, 238, 239, 240, 241, 197, 194; 428/515, 407

[56] References Cited

U.S. PATENT DOCUMENTS

| | | | |
|---|---|---|---|
| 3,101,275 | 8/1963 | Cairns et al. | 427/307 |
| 3,617,344 | 11/1971 | Leininger et al. | 117/47 |
| 3,632,387 | 1/1972 | Sutherland | 117/47 A |
| 3,966,580 | 6/1976 | Janata et al. | 427/307 |
| 4,291,133 | 9/1981 | Horak et al. | 525/74 |

*Primary Examiner*—Carman J. Seccuro
*Attorney, Agent, or Firm*—Oblon, Fisher, Spivak, McClelland & Maier

[57] ABSTRACT

Polymers, the surfaces of which have been modified, are disclosed. The polymer surface is modified by embedding therein a second polymer. The modified polymer substantially retains its bulk properties while also possessing, at its surface, properties of the second polymer.

20 Claims, 4 Drawing Figures

SURFACE MODIFIED POLYMERS

CROSS-REFERENCE TO RELATED APPLICATIONS

This application is a continuation-in-part of our application Ser. No. 027,366 filed Apr. 5, 1979 now U.S. Pat. No. 4,291,133, which is relied upon and incorporated by reference herein.

FIELD OF INVENTION

For various applications, many of the industrially manufactured polymers possess the desirable characteristics with respect to bulk properties, such as chemical and mechanical stability, elasticity, thermoplasticity, etc., but are deficient with respect to the characteristics of their surfaces. Such deficiencies include lack of biocompatibility, thrombogeneity, lack of wettability by water and polar solvents, incapacitance to accommodate chemical charges and to interact or react with chemical substrates of particular interest. In order to correct such deficiencies, the more rational approach is the surface modification of such polymers rather than the development of new polymers with the desired surface characteristics but unknown bulk properties. A common remedy for the above stated surface deficiencies is introduction of specific polar groups into such polymer surfaces.

Polar functional groups have been introduced to the polymer surfaces by chemical methods, such as chromium trioxide oxidation, physical methods, such as corona treatment, and via introducing small functionalized molecules to the surface. In the later case, the long aliphatic chains of tridodecyl methyl ammonium chloride were absorbed into the swollen surface of the polymer to be modified leaving polar function group at the surface. The polar groups were responsible for a limited ion exchange capacity of the modified polymer surface [Froehling, et al., Journal of Applied Polymer Science, Vol. 21, 2855-2859 (1977)]. This process is disclosed in U.S. Pat. No. 3,617,344 of Leininger, et al.

SUMMARY OF THE INVENTION

The invention is directed to modification of polymers to make their hydrophobic surfaces better suited in specific applications due to, for example, their modified wettability, chemical reactivity, adsorption and ion exchange capacity and modified dielectric characteristics. Such properties make the polymers with the modified surfaces useful in biomedical application (resulting from improved biocompatibility), chromatography (resulting from adsorption and ion exchange capacities), as matrices for immobilization of various substrates and reagents (resulting from chemical reactivity of the surface), useful in clinical laboratories, etc. The general surface modification will be a procedure allowing introduction of any desired functionality to the surface and the modification will result in a stable network with practically no effect on the bulk properties of the polymer.

The modification procedure is based on experimental observations supported by new theoretical concepts. The modification procedure exploring absorption of small molecules such as tridodecyl methyl ammonium chloride by the swollen surface of a polymer to be modified (vide supra) has resulted in a limited ion exchange capacity of the modified surface. The limited capacity is caused most probably by the quaternary ammonium nitrogen not communicating with the surrounding medium as the molecules of the modifier penetrate too deep into the swollen surface of the polymer. The substitution of a small molecular modifier with a macromolecular modifier proposed in this application eliminates this problem. The polymer modifier carrying polar functional groups and the polymer substrate interact at the interface of the swollen surface and the surrounding solution containing the polymer modifier only. As the two polymers are virtually incompatible, the swollen surface of the substrate polymer allows limited penetration of long aliphatic side chains of the polymer modifier and their trapping after depleting the surface of the solvent.

Generally speaking, such modification of the substrate polymer is achieved by physically penetrating its surface with a second polymer which has a substantially linear backbone, which has pendant aliphatic chains along said backbone and which also contains reactive sites otherwise referred to as functional groups. Modification of the substrate polymer involves penetration of its surface by the regularly positioned pendant aliphatic side chains of the second polymer. In one embodiment, modification of the polymer involves swelling the surface of the polymer to be modified and allowing the aliphatic side chains of said second polymer to penetrate that surface.

The principles of the invention will be illustrated by the following.

DESCRIPTION OF THE DRAWINGS

FIG. 1 depicts a polymer modified in accordance with the invention and exhibiting maximum stability, compared to the similar polymer networks with some of the side chains being not anchored (free).

Figure 1:
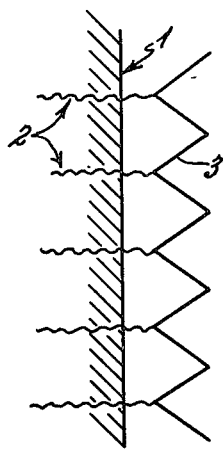
In FIG. 1 of the Drawings, the swollen surface (1) of the polymer substrate to be modified has absorbed a maximum number of aliphatic side chains (2) attached to the backbone (3) of the polymer modifier. Thus.
Figure 2:
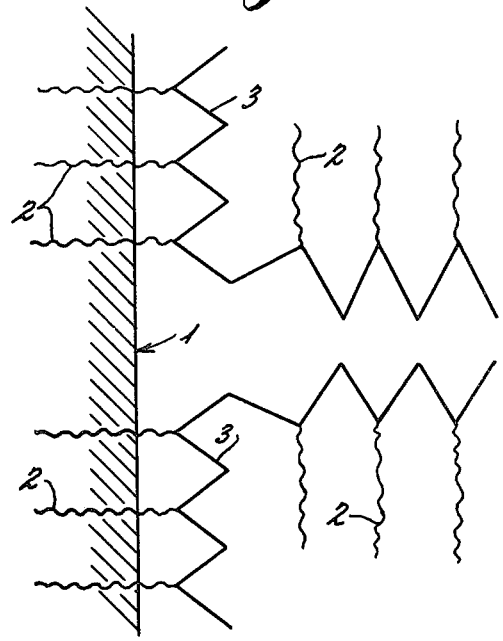
In FIG. 2, only a portion of the macromolecules of the modifier had been attached to the surface via side chains with the remaining portion of the molecule experiencing a high degree of freedom.
Figure 3:
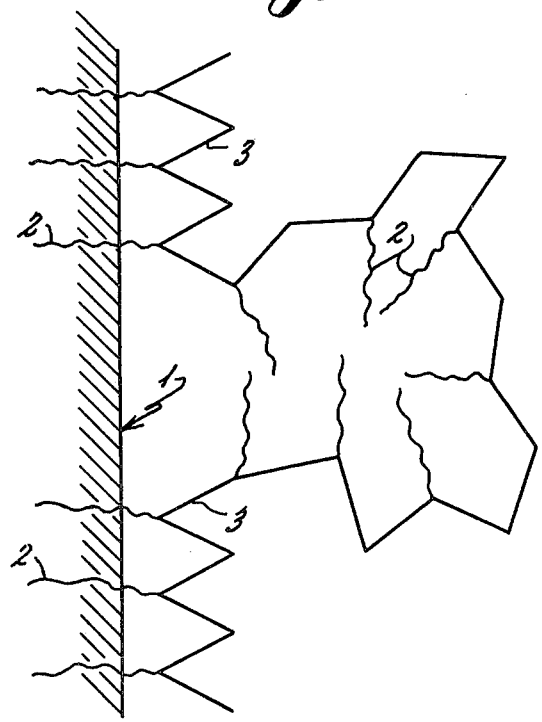
FIG. 3 depicts another polymer network with an incompletely attached molecule of the modifying polymer, which forms loops, in which the side chains form a lipophilic core.

The polymeric networks represented in FIGS. 2 and 3 exhibit the additional characteristics, compared to the network represented in FIG. 1 resulting from the special properties, of the portion of the modifying polymer which remains unattached.

Figure 4:
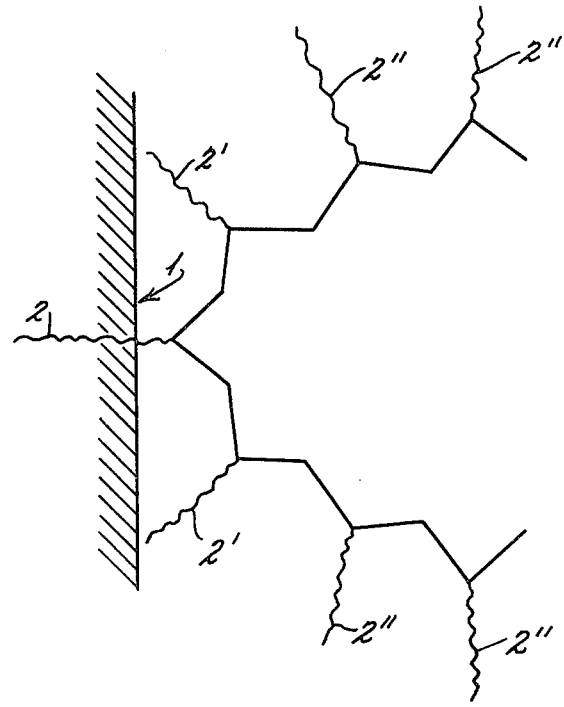

The interaction of the swollen surface of the polymer may be referred to as a "zip-in" mechanism, which is represented in FIG. 4: the chain (2) trapped in the swollen surface (1) directs the absorption of neighboring chains (2') prior to absorption of other more distant chains (2''). This concept is supported by basic principles of dynamic stereochemistry and by probability considerations. Likewise, those principles and considerations support the prediction of stability of the modified polymers of the invention. That is, the escape and reabsorption of a single aliphatic chain from the modified surface is more probable than is escape of a multiplicity of the aliphatic side chains and substantial detachment of the polymer modifier. The spontaneous escape of aliphatic chains from the unswollen surface is improbable.

DETAILED DESCRIPTION OF THE INVENTION

A surface-modified polymeric substrate in accordance with the invention results from the interaction of the polymer substrate swollen surface with a polymer modifier. The polymer modifier is a branched chain polymer (or copolymer) which has a substantially linear backbone, contains reactive sites which are also referred to herein as functional groups and contains aliphatic side chains. The polymeric substrate surface becomes modified by penetration of its surface by the aliphatic side chains of the polymer modifier which become embedded in the polymer subtrate. It is the reactive sites of the polymer modifier which substantially alter the surface characteristics of the polymer substrate.

The polymer substrate which becomes surface-treated in accordance with the invention is generally hydrophobic and swellable by solvent action. By way of example, the polymer substrate may be polyethylene, polypropylene, or polyvinylchloride and copolymers thereof, or rubber and elastomers such as polybutadiene, polystyrene, or polyacrylonitrile and copolymers thereof.

The polymer modifier has a substantially linear backbone. Its aliphatic side chains depending or pendant from that backbone are preferably of the same length. The ideal chain length of the aliphatic pendant is between $C_8$ and $C_{20}$; side chains of this length allow fast and sufficiently deep penetration into the swollen surface of the polymer substrate.

The spacing between two pendant aliphatic groups will determine to some extent the degree to which the linear polymer backbone is anchored to the surface. The spacing between aliphatic groups should be sufficient to match the capacity of the surface to accommodate each neighboring chain. However, if such spacing is too great, the plural anchoring effect may be decreased. Generally, it is preferred that the spacing between pendant aliphatic groups range from a length corresponding to from about three to about ten carbon atoms. Preferably, the aliphatic chains are substantially regularly spaced along said backbone. The molecular weight of the polymer modifier may vary widely and by way of illustration, can vary from about 1,000 to about 30,000.

The polymer modifiers may be divided into two groups based on the position of the reactive sites or functional groups: those in which the reactive site or functional group is in the polymer backbone and those in which the reactive site or functional group is pendant from the polymer backbone. The functional groups may be primary, secondary or tertiary amino; amido; N-alkyl substituted amido wherein the alkyl can contain up to about 18 carbon atoms, phosphine, carbamate, ethers, ester or carboxylates. The functional groups can be hydrophilic, charged containing positive and/or negative ions, and/or chelating agents and can render the modified polymer biocompatible and chemically reactive. The aliphatic chains of the polymer modifier can be, but of course need not be, a part of a functional group on the polymer modifier.

Accordingly, polymers can be used to modify the polymer substrate, in accordance with the invention, which contain the functional group in the backbone of the polymer include poly(n-alkyl ethyleneimines), polymeric phosphines, N-alkyl substituted nylons, polycaprolactams and polyurethanes which contain the recurring units of formulae I–IV:

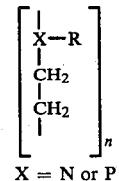

I

X = N or P

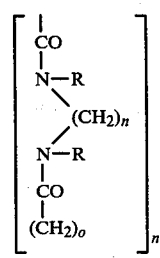

II

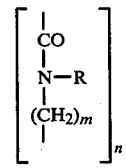

III

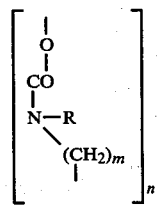

IV

The polymer modifier may be either a polymer or a copolymer containing the units of formulae I–IV. The aliphatic side chains of the polymer modifier may in fact be a substituent of the functional group in the polymer modifier; thus in any one of formulae I–IV, R may be an alkyl of 8 to 20 carbon atoms. In formulae I–IV, R may be selected from the group consisting of H; alkyl of about 8 to 20 carbon atoms or substituted alkyl of up to about 20 carbon atoms, such as —CH$_2$CH$_2$CN; and n may be an integer of 5 to 100. The distance between aliphatic chains in the polymer modifier may be controlled in different ways. One way involves controlling the number of atoms in the recurring unit(s), that is, in the monomer or comonomeric fragments, between the aliphatic side chains. A second way to control the distance between aliphatic chains on the polymer modifier is during alkylation or N-alkylation reactions of precursors of the polymer modifier, for example, a precursor containing unit(s) of formulae I–IV in which R=H, to measure and control the (R=H)/(R=alkyl) ratio. N-alkylation reactions of polymer modifier precursors in which R is H may result in a polymer containing NH groups, and, of course, such NH groups may be subjected to subsequent reactions, as for example with acrylonitrile.

Functional groups pendant from the polymer backbone may be ether, OR'; carboxylates, COOR'; ester groups OC(O)R', wherein R' may be hydrogen, alkyl of up to 20 carbon atoms or substituted alkyl of up to 20 carbon atoms. Accordingly, formulae V–VIII represent units of monomer or comonomer fragments which may be recurring units in polymer modifiers in which the functional group is pendant and depending from the polymer modifier backbone. Although the long chain aliphatic groups of the polymer modifier may be independent of said functional group and depend from a carbon atom of the polymer modifier backbone, the long chain aliphatic groups may be a part of the functional groups of the polymer modifier.

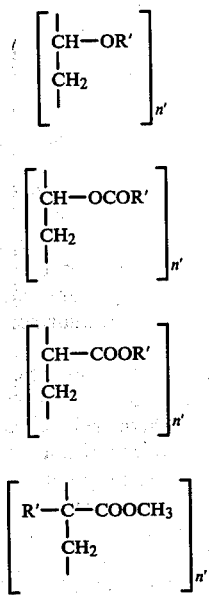

In the foregoing formulae V–VIII, R' is a long aliphatic chain such as an alkyl of 8 to 20 carbon atoms; and n' is an integer of from 5 to about 200. After the substrate polymer has been modified by, for instance, any one of the polymers containing such recurring pendant functional groups, the modified polymer may be subjected to subsequent reactions. For example, these subsequent reactions include cleavage of the O—C bonds of ether and ester group. Such reactions include standard organic synthesis procedures. This is particularly interesting regarding structures V, VI, and VII for which this step would provide for yet another type of modified surfaces; by hydrolysis, the polymer backbone of the polymer modifier can be detached from the modified polymer, leaving long chain aliphatic acids and alcohols immobilized on the surface.

The modified polymers of the invention are presently made by swelling the substrate polymer and then modifying the swollen substrate polymer by allowing the aliphatic chains of the polymer modifier to penetrate the surface of the swollen polymer substrate. It is necessary to use a solvent system, during the stage in which modification takes place, in which the polymer modifier is soluble and in which the polymer substrate remains swollen, to attain maximum stability in the newly developing network. In case the polymer modifier is soluble in a solvent different from that which is used to swell the polymer substrate to be modified, a mixture of two or more solvents may be used to effect the modification of the substrate polymer. In such a solvent mixture, at least one solvent acts to solubilize the polymer modifier and at least one other solvent acts to swell the substrate polymer or to maintain the swollen polymer in the swollen state. Thus, the method of surface modification can be undertaken in two stages: in the first stage, the substrate polymer is incubated in solvent(s) acting as a swelling agent, and in the second stage, the swollen polymer substrate is incubated in a solution of the polymer modifier. When crystalline polymers are employed, incubation is enhanced by elevated temperatures close to the respective transition temperature.

Solvents which will swell the common hydrophobic polymer substrates are known. The following are examples. Polyethylene and polypropylene surfaces will swell in chlorobenzene, orthodichlorobenzene, and the like. Toluene and hexane can be used to swell polyvinylchloride.

The degree to which surface absorption by the polymer substrate takes place depends on the swelling power of the solvent, the concentration of the modifying polymers in the solvent and time of exposure and the temperature of the solvent. The degree of absorption can be controlled by regulating such variables. For example, high concentrations of polymer modifier in the solvent system can lead to polymer networks, as depicted in FIGS. 2 and 3. The ratio of polymer modifier and polymer substrate may range between 1 to 100 to 1 to 100,000 (W:W), and the concentration of the polymer modifier in solution from 0.01% up to 1%, providing the solubility is not lower.

Introduction of functional groups of the polymer modifier to an otherwise hydrophobic, uncharged, unreactive bioincompatible polymer substrate can render the polymer substrate hydrophilic, charged, chelating, biocompatible and/or chemically reactive. The functional groups of the modified polymer network of the invention may be those of the polymer modifier or derivatives of the functional groups of the polymer modifier produced by chemical reactions occurring subsequent to the basic modification procedure. The selection of the functional groups and the polymer modifiers containing them for the modification method itself is limited by the polarity of the functional group. That is, ionomers carrying highly polar groups, such as those containing ions, may be insoluble in those solvents which swell the polymer substrate. Accordingly, extremely polar functional groups are created at the modified substrate surface in reactions subsequent to the modification procedure. For instance, quaternary ammonium groups can be formed at the modified polymer surface containing tertiary amino groups by known alkylation reactions.

The results of the modification procedure can be tested by any of the methods used for analysis of polymer surfaces. From these, the wettability tests, more specifically, the contact angles, are well suited for generally characterizing the introduction of polar groups onto the hydrophobic surface of polymer substrates.

EXAMPLES

The following examples are presented to illustrate and to explain the invention.

EXAMPLE 1

Poly(vinylchloride) beads, high molecular weight [10 g; Aldrich Co., Cat. No. 18,956-1] were incubated in 200 ml of toluene solution containing 2 g of poly(hexadecylmethacrylate) [prepared from a 19% solution in toluene by dilution; Aldrich Co., Cat. No. 18,210-9] for 10 hrs. at ambient temperature. Then 100 ml of isopropylalcohol was added and the beads were separated by suction filtration after standing an additional 2 hrs. Then the beads were washed with a mixture of toluene-isopropylalcohol (50 ml, 1:1, v;v) and twice with isopropylalcohol (100 ml total). The suction was continued until dry appearance and then air-dried for 24 hrs at ambient temperature in form of a thin layer over a filter paper.

EXAMPLE 2

Poly(ethylene) pellets, high density [10 g; Scientific Polymer Products, Inc., Cat. No. 041] were incubated in 250 ml colution containing 2 g of poly(hexadecylmethacrylate) used [19% solution in toluene; Aldrich Co., Cat. No. 18, 210-9] in cyclohexane at the boiling temperature of the solution for 2 hrs. After cooling down to ambient temperature (⅜ hr), 50 ml of isopropylalcohol was added and the mixture was allowed to stand for 2 hrs. The pellets were separated by suction filtration, washed with a mixture of toluene-isopropylalcohol (50 ml, 1:1, v:v) and then twice with isopropylalcohol (100 ml total). The suction was continued until dry appearance and then air-dried for 24 hrs at ambient temperature in form of a thin layer over a filter paper.

What is claimed is:

1. A hydrophobic polymer having a modified surface prepared by a process comprising:
    (a) contacting said surface with a swelling solvent capable of swelling said polymer, whereby a swollen polymer surface is formed,
    (b) contacting said swollen polymer surface with a solution of a second polymer while maintaining said swollen polymer surface in a swollen state, said second polymer having a substantially linear backbone and a plurality of substantially linear aliphatic chains depending from and spaced along said backbone and a plurality of reactive groups as part of the polymer backbone or pendant from said polymer backbone wherein said reactive groups are selected from the group consisting of primary, secondary, and tertiary amino; amido, N-alkyl substituted amido, phosphine, carbamate, ether, ester, carboxylate, and combinations thereof, whereby said second polymer becomes bound to said polymer surface, and
    (c) removing said swelling solvent from said swollen polymer surface.

2. The surface-modified polymer of claim 1, wherein each of said aliphatic chains has at least about five carbon atoms.

3. The surface-modified polymer of claim 1 wherein said second polymer has aliphatic chains substantially regularly spaced from one another.

4. The polymer of claim 1 wherein said pendent aliphatic chains on said second polymer are bound to said polymer backbone by hydrolyzable linkages, and after said second polymer is bound to the surface of said substrate polymer, said linkages are hydrolyzed.

5. The surface-modified polymer of claim 1, wherein said second polymer has at least about ten aliphatic chains.

6. The surface-modified polymeric substrate of claim 1, wherein said aliphatic chains contain at least about five carbon atoms.

7. A process for modifying a substrate hydrophobic polymer surface comprising:
    (a) contacting said surface with a swelling solvent capable of swelling said polymer, whereby a swollen polymer surface is formed,
    (b) contacting said swollen polymer surface with a solution of a second polymer while maintaining said swollen polymer surface in a swollen state, said second polymer having a substantially linear backbone and a plurality of substantially linear aliphatic chains depending from and spaced along said backbone and a plurality of reactive groups as part of the polymer backbone or pendant from said polymer backbone wherein said reactive groups are selected from the group consisting of primary secondary, tertiary amino; amido; N-alkyl substituted amido, phosphine, carbamate, ether, ester, carboxylate and combinations thereof, whereby said second polymer becomes bound to said polymer surface, and
    (c) removing said swelling solvent from said swollen polymer surface.

8. The process of claim 7 wherein said pendent aliphatic chains on said second polymer are bound to said polymer backbone by hydrolyzable linkages, and after said second polymer is bound to the surface of said substrate polymer, said linkages are hydrolyzed.

9. A process for modifying the surface of a hydrophobic polymer, comprising
    swelling said polymer and maintaining said polymer in the swollen state under the following conditions:
        embedding the aliphatic side chains of a second polymer in the surface of said swollen polymer wherein said second polymer has a substantially linear backbone and substantially linear aliphatic side chains depending from and spaced along said backbone and a plurality of reactive groups as part of the polymer backbone or pendant from said polymer backbone wherein said reactive groups are selected from the group consisting of primary, secondary, and tertiary amino; amido, N-alkyl substituted amido, phosphine, carbamate, ether, ester, carboxylate and combinations thereof,
    by treating the swollen polymer with a solution of said second polymer containing amounts of said second polymer effective to allow said second polymer to penetrate and embed the surface of said swollen polymer.

10. A hydrophobic polymer having a modified surface prepared by a process comprising:
    swelling said polymer and retaining said polymer in the swollen state under the following conditions:
        embedding the aliphatic side chains of a second polymer in the surface of said swollen polymer, wherein said second polymer has a substantially linear backbone and substantially linear aliphatic side chains depending from and spaced along said backbone and a plurality of reactive groups as part of the polymer backbone or pendant from said polymer backbone wherein said reactive groups are selected from the group consisting of primary, secondary, tertiary amino; amido; N-alkyl substituted amido, phosphine, carbamate, ether, ester, carboxylate, and combinations thereof, by treating the swollen polymer with a solution of said second polymer containing amounts of said second polymer effective to allow said second polymer to penetrate and embed the surface of said swollen polymer.

11. The surface-modified polymer of claim 10, wherein each of said aliphatic chains has at least about five carbon atoms.

12. The surface-modified polymer of claim 10 wherein said second polymer has aliphatic chains substantially regularly spaced from one another.

13. The surface-modified polymer of claim 10, wherein said second polymer has at least about ten aliphatic chains.

14. The surface-modified polymer of claim 10, wherein said aliphatic chains contain at least about five carbon atoms.

15. A surface-modified polymeric substrate comprising
    (1) a hydrophobic polymeric substrate, and
    (2) a second polymer having a substantially linear backbone and substantially linear aliphatic side chains depending from and spaced along said backbone and a plurality of reactive groups as part of the polymer backbone or pendant from said polymer backbone wherein said reactive groups are selected from the group consisting of primary, secondary, or tertiary amino; amido; N-alkyl substituted amido, phosphine, carbamate, ether, ester, carboxylate, and combinations thereof, wherein said aliphatic side chains are embedded in said polymeric surface.

16. The surface-modified polymeric substrate of claim 15, wherein said aliphatic chains contain at least about five carbon atoms.

17. The surface-modified polymeric substrate of claim 15, wherein (1) is swellable.

18. The surface-modified polymeric substrate of claim 15, wherein each of said aliphatic chains has at least about five carbon atoms.

19. The surface-modified polymeric substrate of claim 15 wherein said second polymer has aliphatic chains substantially regularly spaced from one another.

20. The surface-modified polymeric substrate of claim 15 or claim 19, wherein said second polymer has at least about ten aliphatic chains.

* * * * *